United States Patent [19]

Inoue et al.

[11] Patent Number: 5,057,620

[45] Date of Patent: Oct. 15, 1991

[54] PROCESS FOR PRODUCING LINEAR ORGANOTETRASILOXANE HAVING A SILANOL RADICAL AT BOTH ENDS THEREOF

[75] Inventors: Yoshio Inoue; Naoki Omura, both of Annaka, Japan

[73] Assignee: Shin-Etsu Chemical Co., Ltd., Tokyo, Japan

[21] Appl. No.: 563,330

[22] Filed: Aug. 7, 1990

[30] Foreign Application Priority Data

Aug. 8, 1989 [JP] Japan ........................ 1-205082

[51] Int. Cl.$^5$ ........................ C07F 7/08

[52] U.S. Cl. ........................ 556/459

[58] Field of Search ........................ 556/459

[56] References Cited

U.S. PATENT DOCUMENTS

| | | | |
|---|---|---|---|
| 2,600,307 | 6/1952 | Lucas et al. | 556/459 |
| 2,863,897 | 12/1958 | Webrly | 556/459 |
| 3,309,390 | 3/1967 | Omitaushi | 556/459 |
| 3,355,474 | 11/1967 | Wheeler | 556/459 |
| 3,903,047 | 9/1975 | Ashby | 556/459 X |
| 4,287,353 | 9/1981 | Bluestein | 556/459 |
| 4,609,751 | 9/1986 | Hajjar | 556/459 X |
| 4,855,472 | 8/1989 | Burkhardt | 556/459 |
| 4,902,813 | 2/1990 | Wegehaupt et al. | 556/459 |

*Primary Examiner*—Paul F. Shaver

*Attorney, Agent, or Firm*—Oblon, Spivak, McClelland, Maier & Neustadt

[57] ABSTRACT

A process for producing a linear organotetrasiloxane comprises the step of hydrolyzing a dihalotetrasiloxane in the presence of an organic compound having at least one epoxy radical. The process prevents effectively the by-production of high molecular weight or cyclic condensates, and yields a linear organotetrasiloxane having a high OH number and high activity.

7 Claims, 6 Drawing Sheets

PROCESS FOR PRODUCING LINEAR ORGANOTETRASILOXANE HAVING A SILANOL RADICAL AT BOTH ENDS THEREOF

BACKGROUND OF THE INVENTION

1. Field of the Invention

This invention relates to a process for producing a linear organotetrasiloxane with a low molecular weight which has a silanol radical at both ends thereof.

2. Description of the Prior Art

Heretofore, silanol-terminated, low molecular weight linear polysiloxanes have been produced by hydrolyzing a linear organotetrasiloxane having a chlorine atom at both ends thereof in a weakly alkaline aqueous solution.

There is also known a method of producing the above-mentioned polysiloxane by acetoxylating or alkoxylating the above-mentioned organochloropolysiloxane by use of acetic acid or alcohol and hydrolyzing the acetoxylated or alkoxylated compound.

The former method in which hydrolysis of an organochloropolysiloxane is carried out in an weakly alkaline aqueous solution, however, has a problem associated with instability of the silanol radicals to acid or alkali. The problem is that, during hydrolysis, a condensation reaction is caused by the alkali or by HCl arising from the hydrolysis, and, as a result, the formation of the intended organopolysiloxane is accompanied by the formation of organosiloxanes with higher molecular weights or cyclic polysiloxanes. It is very difficult to separate the intended linear organotetrasiloxane with a low molecular weight from the by-produced organopolysiloxanes.

In the latter method in which the intended compound is produced through acetoxylation or alkoxylation, on the other hand, acetoxy or alkoxy radicals are left in the product.

SUMMARY OF THE INVENTION

It is accordingly an object of this invention to provide a process for producing, in a high yield, a linear organotetrasiloxane with a low molecular weight which has a silanol radical at both ends thereof.

This invention accomplishes the production of the intended organotetrasiloxane in a high yield, by hydrolysis in the presence of an organic compound having at least one epoxy radical.

According to this invention, there is provided a process for producing an organotetrasiloxane represented by the following general formula (I):

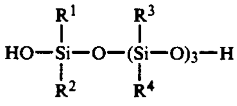
(I)

wherein X represents a halogen atom such as a fluorine atom chlorine atom, bromine atom and iodine atom, and $R^1$, $R^2$, $R^3$ and $R^4$, which may be identical or different, each represent a univalent substituted or unsubstituted hydrocarbon radical of 1 to 10 carbon atoms, which process comprises the step of hydrolyzing a dihalotetrasiloxane represented by the following general formula (II):

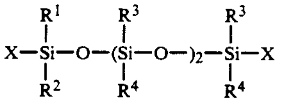
(II)

wherein $R^1$, $R^2$, $R^3$ and $R^4$ are as defined above, in the presence of an organic compound having at least one epoxy radical.

According to the invention as above, it is possible to obtain a linear organotetrasiloxane of the above general formula (I) in an extremely high yield, as compared with the prior art.

The linear organotetrasiloxane obtained by the process of this invention contains less by-produced condensates, as compared with the linear organotetrasiloxanes obtained by the conventional methods, and therefore has the advantages of high OH number and high activity.

DETAILED DESCRIPTION OF THE INVENTION

Starting Material

Figure 1:
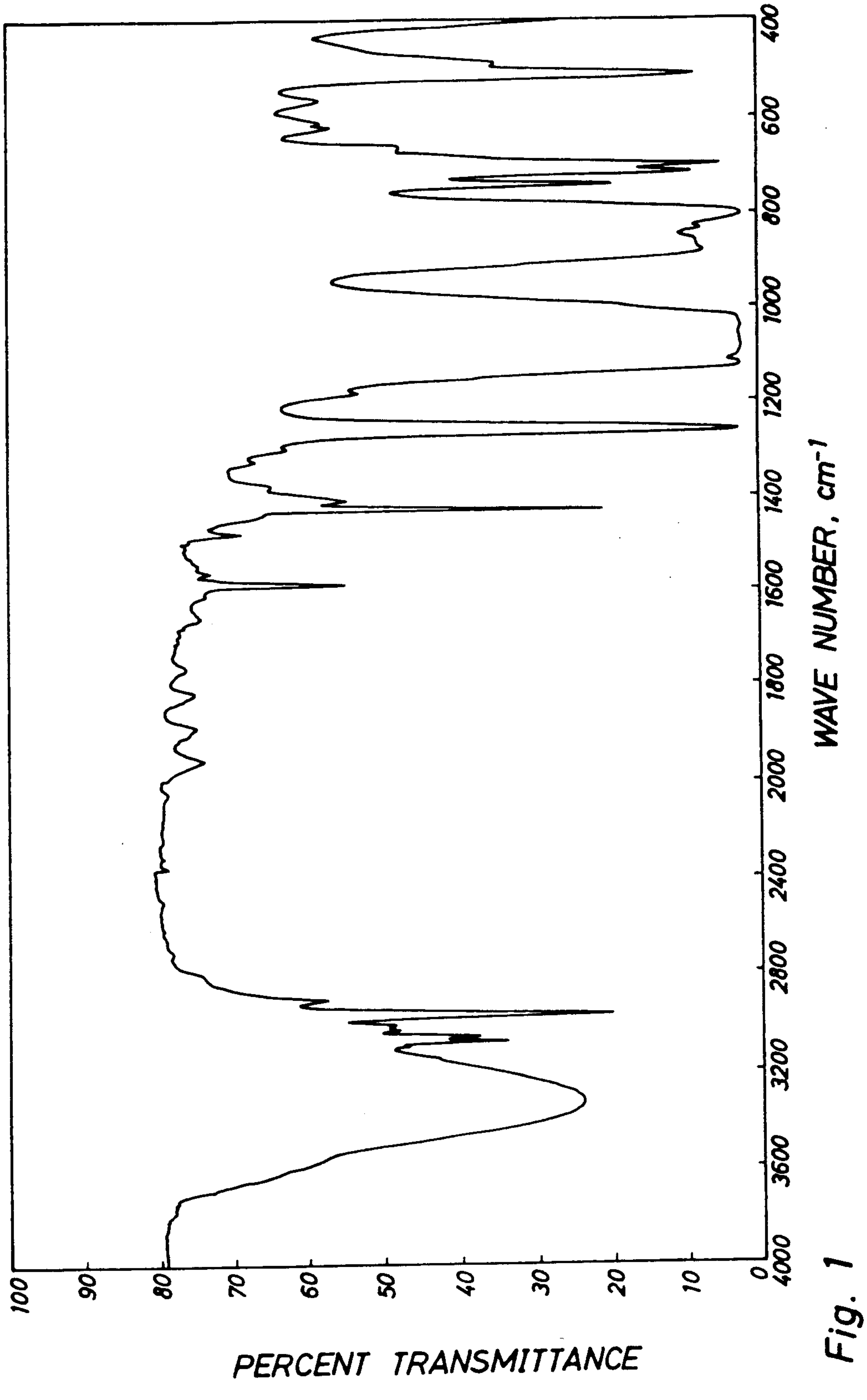
FIGS. 1 to 6 show infrared absorption spectrum charts of organotetrasiloxanes obtained in Examples 1 to 6, respectively.

In the process of this invention, a dihalotetrasiloxane represented by the above-mentioned general formula (II):

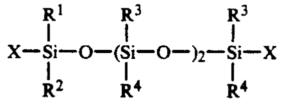
(II)

wherein $R^1$ to $R^4$ are as defined above, is used as a starting material.

Examples of the univalent substituted or unsubstituted hydrocarbon radicals of 1 to 10 carbon atoms, preferably 1 to 8 carbon atoms, $R^1$ to $R^4$, include lower alkyl radicals of up to 8 carbon atoms such as methyl, ethyl, propyl, butyl, etc.; cycloalkyl radicals such as cyclohexyl, etc.; alkenyl radicals such as vinyl, allyl, propenyl, buteny, acryl, etc.; aryl radicals such as phenyl, tolyl, naphthyl, etc.; and radicals corresponding to these radicals in which a part or all of the hydrogen atoms are substituted by halogen atoms, for instance, trifluoropropyl, etc.

Tetrasiloxanes used preferably as the dihalotetrasiloxane in the process of this invention include, but are not limited to, the followings: octamethyl-1,7-dichlorotetrasiloxane, 1,1-diphenylhexamethyl-1,7-dichlorotetrasiloxane, 1-phenylheptamethyl-1,7-dichlorotetrasiloxne, 1,1-diphenyl-3,5,7-trivinyl-3,5,7-trimethyl-1,7-dichlorotetrasiloxane, 1-trifluoropropylheptamethyl-1,7-dichlorotetrasiloxane, 1-phenyl-1-vinylhexamethyl-1,7-dichlorotetrasiloxane, 1,1-diphenyl-7-vinylpentamethyl-1,7-dichlorotetrasiloxane, and 1-vinylheptametyl-1,7-dichlorotetrasiloxane.

The dihalotetrasiloxane described above can be produced by the methods known per se. For example, the dihalotetrasiloxane can be obtained easily by reacting a silane compound represented by the following general formula (III):

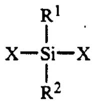
(III)

wherein $R^1$, $R^2$ and X are as defined above, with a cyclic trisiloxane represented by the following general formula (IV):

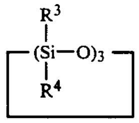
(IV)

in the presence of a catalyst such as hexamethylphosphoric amide.

Organic Compound Having an Epoxy Radical

The term, epoxy radical, herein means the radical having the formula:

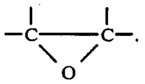

In the process of this invention, the organic compound having at least one epoxy radical to be used in hydrolysis may be, for example, propylene oxide, butylene oxide, epichlorohydrin, butadiene diepoxide or the like, at least one of which is used either singly or in combination. Especially, propylene oxide is used preferably.

The epoxy-containing organic compound functions to capture HCl which is formed, for example, upon hydrolysis. As a result, the silanol radicals formed are prevented from condensation reaction.

The epoxy-containing organic compound is used in an amount of at least 1 mol, particularly from 3.0 to 4.0 mol, per mol of the Si-X radical in the dihalotetrasiloxane represented by the general formula (II) above.

Hydrolysis

In this invention, a dihalotetrasiloxane of the above general formula (II) is hydrolyzed to yield the intended linear organotetrasiloxane.

The hydrolysis is carried out by the usual method of simply mixing the dihalotetrasiloxane with water, except for the presence of the epoxy-containing organic compound described above. Since it is unnecessary to add an alkali as a neutralizing agent, which has been required in the prior art, the silanol radicals (Si-OH) can be prevented from performing condensation with each other.

The hydrolysis is preferably carried out in the hydrogen ion concentration range of pH 6 to 8. The amount of water used for the hydrolysis is from 1.0 to 2.0 mol, particularly from 1.0 to 1.2 mol, per mol of the Si-H radicals in the dihalotetrasiloxane serving as the starting material. The hydrolyzing temperature is preferably from 0° to 20° C.

Linear Organotetrasiloxane

According to this invention, the hydrolyzate obtained as above is treated in a conventional manner to obtain a linear organotetrasiloxane having a silanol radical at both ends thereof, represented by the above-mentioned general formula (I):

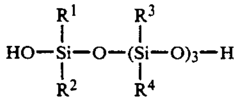
(I)

The organotetrapolysiloxane, per se, is useful as an aid in processing rubbers, a wetting agent for rubbers, and so on. Also, the organotetrasiloxane is suitable for use as a compounding agent in silicone hard coating materials, paper release coating materials, release emulsion, room temperature curable silicone rubbers, etc. Furthermore, the organotetrasiloxane is useful as an intermediate for production of silicone oils, silicone resins, and so on.

This invention will be further described by the following non-limitative examples.

EXAMPLES

EXAMPLE 1

A 2 liter round bottom flask equipped with a dropping funnel, a water condenser and a mechanical stirrer was charged with 689 g (11.9 mol) of propylene oxide and 72 g (4.0 mol) of water, and the contents of the flask were stirred for 10 minutes at room temperature and normal pressure.

Next, 855 g (1.8 mol) of 1,1-diphenyl-3,3,5,5,7,7-hexamethyl-1,7-dichlorotetrasiloxane was added dropwise to the flask, with ice cooling, over 3 hours so as not to raise the temperature above 30° C., followed by stirring for 2 hours.

The reaction mixture was then dried over an excess of $MgSO_4$, and filtered. The reaction solution obtained was stripped finally to 80° C. under, 5 mmHg to obtain 700 g of a colorless transparent liquid. The liquid was found by the following analytical results to be 1,1-diphenyl-3,3,5,5,7,7-hexamethyl-1,7-dihydroxytetrasiloxane.

Elemental analysis:

Found: C: 49.0 %; H: 6.90 %; 0: 18.0 %; Si: 25.3 %.

Calcd. for $C_{18}H_{30}O_5Si_4$:

C: 49.2 %; H: 6.89 %; 0: 18.2 %; Si: 25.6 %.

IR absorption spectrum: (shown in FIG. 1)

3700-2800 $cm^{-1}$ (-OH, broad, strong)

2960 $cm^{-1}$ ($-CH_3$, sharp)

1950, 1890, 1830, 1780 $cm^{-1}$ ( 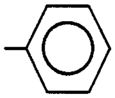 , weak)

1430 $cm^{-1}$ (Si 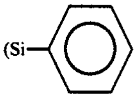 , sharp, strong)

$^1H$ NMR spectrum:

-continued

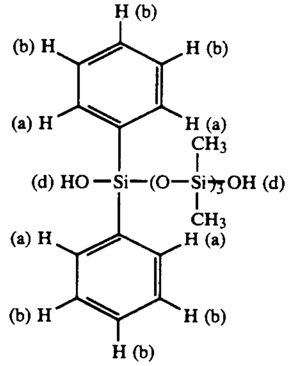

| δ (ppm) | Assignment |
|---|---|
| 7.6 (4H) | a |
| 7.2 (6H) | b |
| 0.1 (18H) | c |
| 5.0-5.4 (2H) | d |

OH number (Grignard method):
0.45 mol/100 g (theoretical: 0.46 mol/100 g)
Refractive index $n_D^{25}$: 1.4973

EXAMPLE 2

The same procedure as in Example 1 was repeated except for using of 536 g (1.3 mol) of 1-phenyl-1,3,3,5,5,7,7-heptamethyl-1,7-dichlorotetrasiloxane, 497.6 g (8.58 mol) of propylene oxide and 51.5 g (2.86 mol) of water, to obtain 414.5 g of a colorless transparent liquid.

The liquid obtained was found by the following analytical results to be 1-phenyl-1,3,3,5,5,7,7-heptamethyl-1,7-dihydroxytetrasiloxane.

Figure 2:
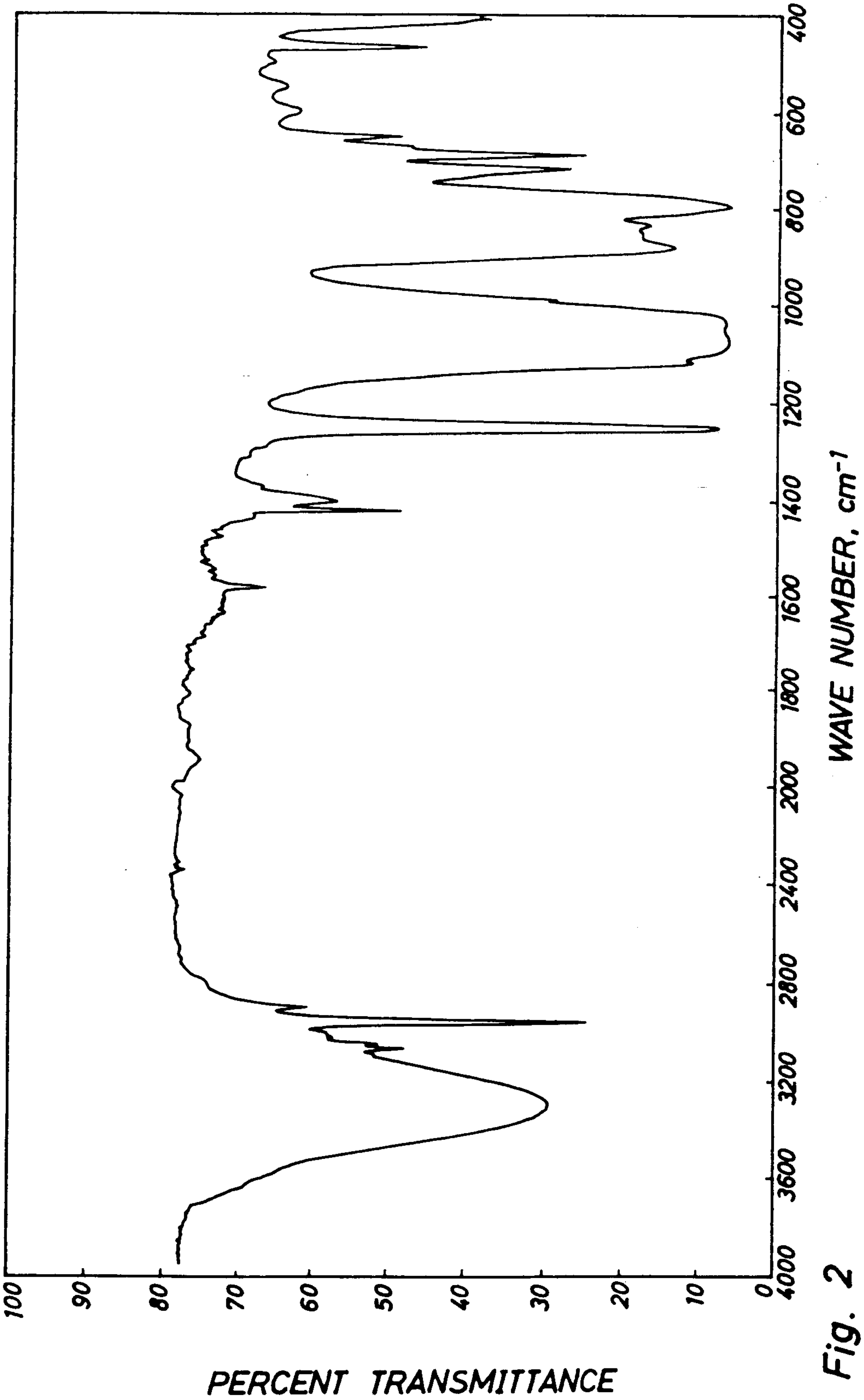

Elemental analysis:
Found: C: 41.1 %; H: 7.50 %; 0: 21.0 %; Si: 29.5 %.
Calcd. for $C_{13}H_{28}O_5Si_4$:
C: 41.4 %; H: 7.49 %; 0: 21.2 %; Si: 29.8 %.
IR absorption spectrum: (shown in FIG. 2)
3700-2800 $cm^{-1}$ (-OH)
2960 $cm^{-1}$ ($-CH_3$)
1580 $cm^{-1}$

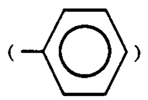

$^1$H NMR spectrum:

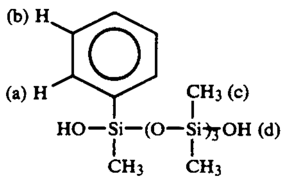

| δ (ppm) | Assignment |
|---|---|
| 7.6 (2H) | a |
| 7.2 (3H) | b |
| 0.1 (21H) | c |
| 5.8-6.2 (2H) | d |

OH number:
0.41 mol/100 g (theoretical: 0.53 mol/100 g)
Refractive index $n_D^{25}$: 1.4534

EXAMPLE 3

The same procedure as in Example 1 was repeated except for using 216.5 g (0.5 mol) of 1-(3,3,3-trifluoropropyl)-1,3,3,5,5,7,7-heptamethyl-1,7dichlorotetrasiloxane, 185.6 g (3.2 mol) of propylene oxide and 19.2 g (1.06 mol) of water, to obtain a colorless transparent liquid.

This liquid was distilled to yield 84.5 g of a colorless transparent liquid having a boiling point of 104° C. under a reduced pressure of 2.5 mmHg.

The liquid obtained was found by the following analytical results to be 1-(3,3,3-trifluoropropyl)-1,3,3,5,5,7,7-heptamethyl-1,7-dihydroxytetrasiloxane.

Figure 3:
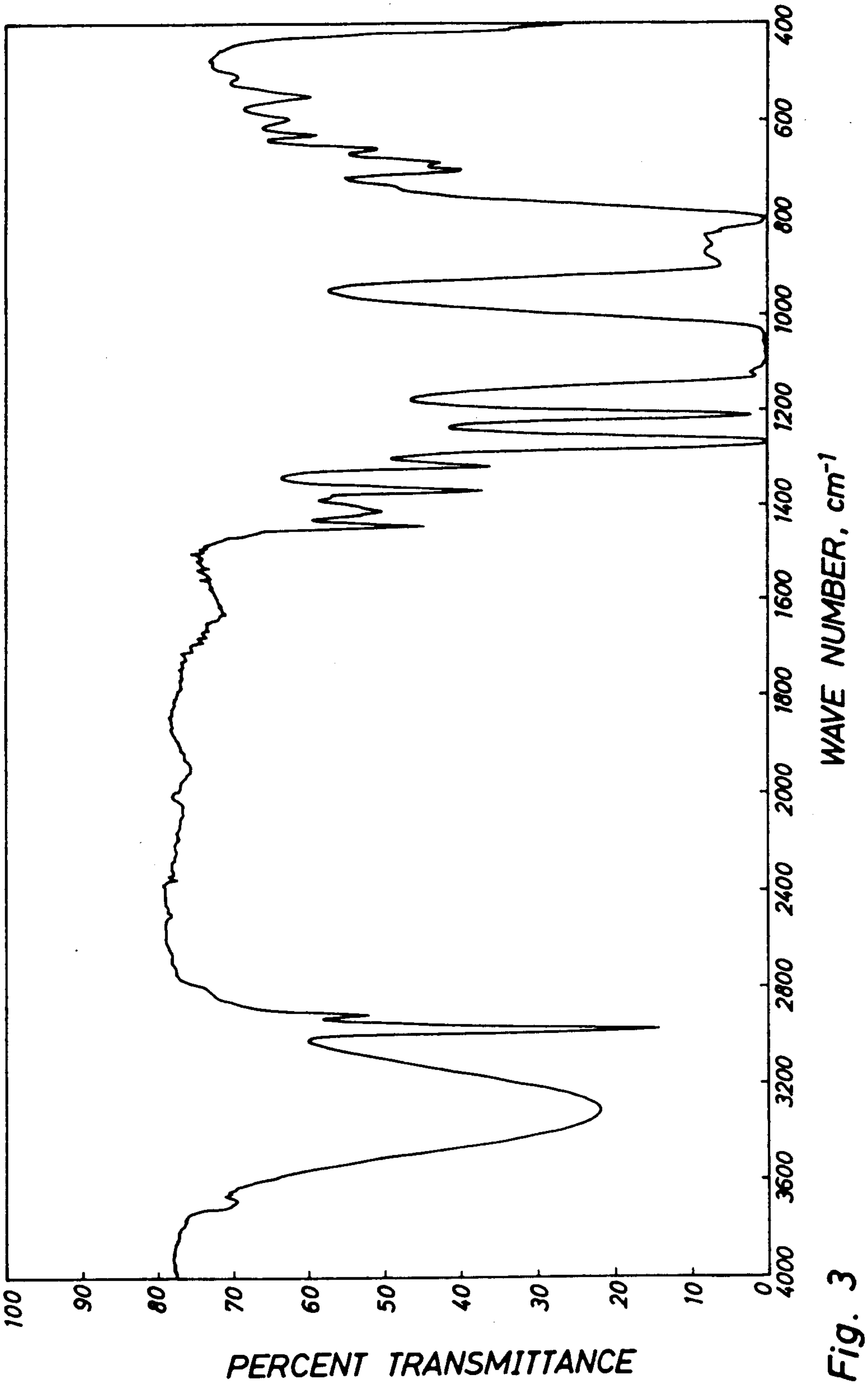

Elemental analysis:
Found: C: 29.8 %; H: 6.84 %; 0: 20.0 %; Si: 27.9 %.
Calcd. for $C_{10}H_{27}O_5Si_4F_3$:
C: 30.3 %; H: 6.86 %; 0: 20.2 %; Si: 28.3 %; F: 14.4 %.
IR absorption spectrum: (shown in FIG. 3)
3700-2800 $cm^{-1}$ (-OH)
1220 $cm^{-1}$ ($-CH_3$)
1220 $cm^{-1}$ ($-CF_3$)

$^1$H NMR spectrum:

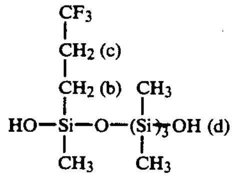

| δ (ppm) | Assignment |
|---|---|
| 0.4 (21H) | a |
| 1.0-1.1 (2H) | b |
| 2.0-2.6 (2H) | c |
| 5.6-6.0 (2H) | d |

OH number: 0.40 mol/100 g (theoretical: 0.50 mol/100 g}
Refractive index $n_D^{25:}$ 1.3920

EXAMPLE 4

The same procedure as in Example 1 was repeated except for using 64.7 g (0.18 mol) of 1-vinyl-1,3,3,5,5,7,7-heptamethyl-1,7-dichlorotetrasiloxane, 68.2 g (1.2 mol) of propylene oxide and 7.1 g (0.39 mol) of water, to obtain a colorless transparent liquid.

This liquid was distilled to yield 80.5 g of a colorless transparent liquid having a boiling point of 105°-110° C. under a reduced pressure of 4 mmHg.

The liquid obtained was found by the following analytical results to be 1-vinyl-1,3,3,5,5,7,7-heptamethyl-1,7-dihydroxytetrasiloxane.

Figure 4:
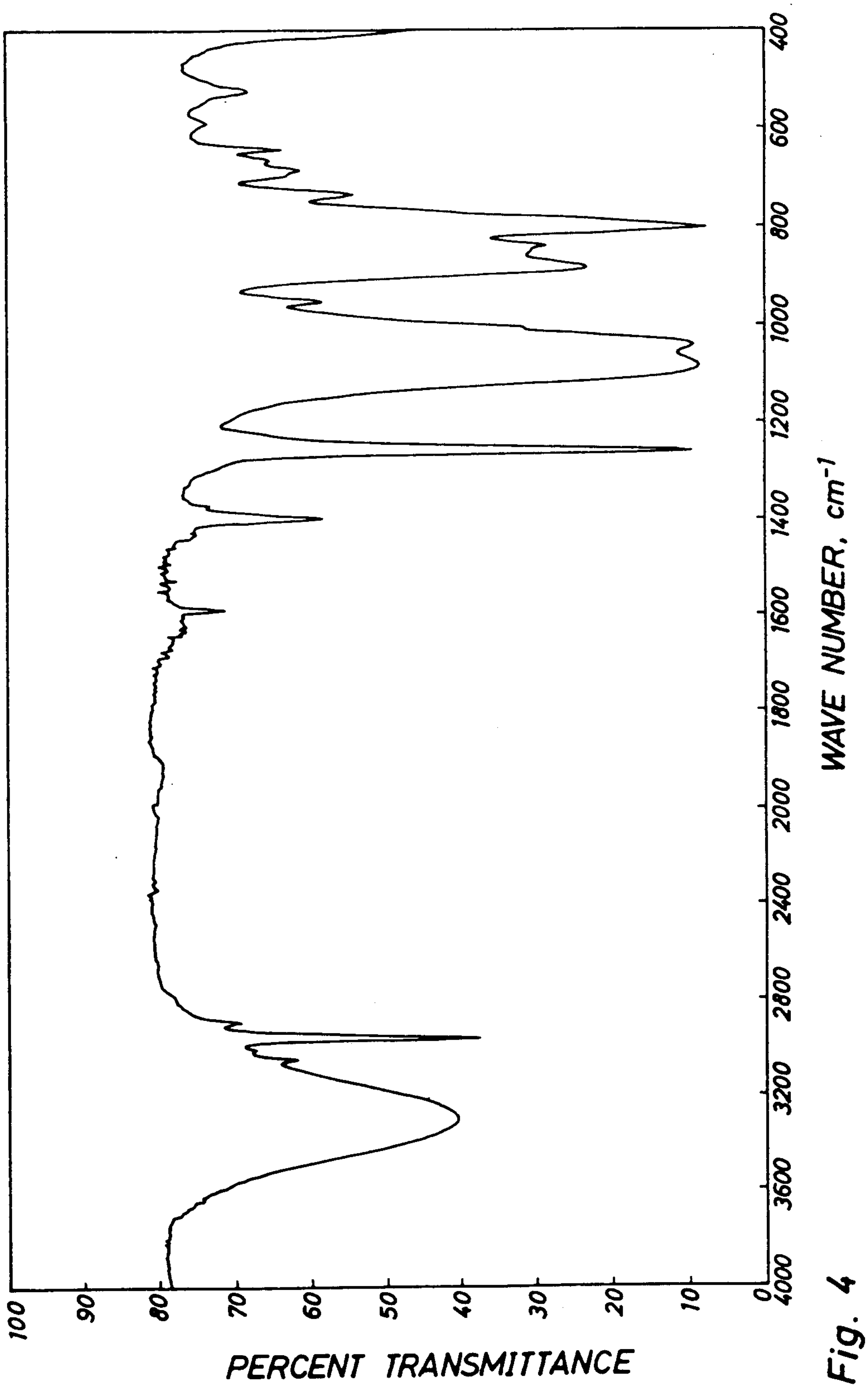

Elemental analysis:
Found: C: 32.8 %; H: 7.99 %; 0: 24.3 %; Si: 34.0 %.
Calcd. for $C_9H_{26}O_5Si_4$:
C: 33.1 %; H: 8.02 %; 0: 24.5 %; Si: 34.4 %.
IR absorption spectrum: (shown in FIG. 4)
3700-2800 $cm^{-1}$ (-OH)
2950 $cm^{-1}$ ($-CH_3$)
1660 $cm^{-1}$ ($-CF_3=CH_2$)

$^1$H NMR spectrum:

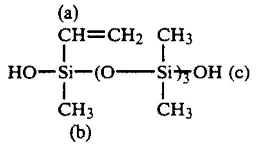

| δ (ppm) | Assignment |
|---|---|
| 6.0 (3H) | a |
| 0.1 (21H) | b |
| 5.7-6.2 (2H) | c |

OH number:
0.58 mol/100 g (theoretical: 0.61 mol/100 g)
Refractive index $n_D^{25}$: 1.4152

EXAMPLE 5

The same procedure as in Example 1 was repeated except for using 613.2 g (1.2 mol) of 1,1-diphenyl-3,5,7-trivinyl-3,5,7-trimethyl-1,7-dichlorotetrasiloxane, 460 g (7.9 mol) of propylene oxide and 47.5 g (2.6 mol) of water, to obtain 370 g of a colorless transparent liquid.

The liquid obtained was found by the following analytical results to be 1,1-diphenyl-3,5,7-trivinyl-3,5,7-trimethyl-1,7-dihydroxytetrasiloxane.

Figure 5:
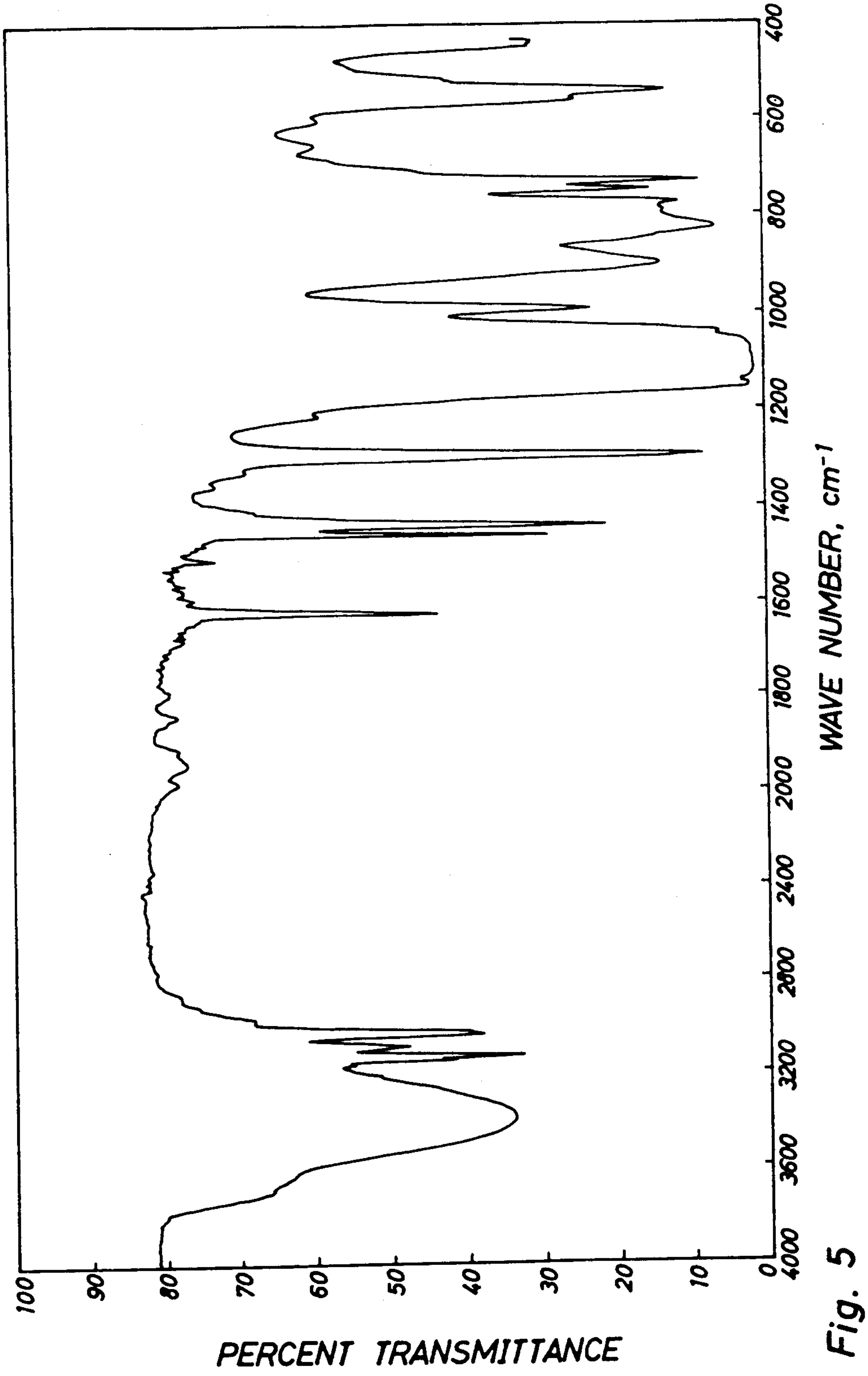

Elemental analysis:
Found: C: 52.8 %; H: 6.40 %; 0: 16.6 %; Si: 23.2 %.
Calcd. for $C_{21}H_{30}O_5Si_4$:
C: 53.1 %; H: 6.37 %; 0: 16.8 %; Si: 23.7 %.
IR absorption spectrum: (shown in FIG. 5)
3800-2800 cm$^{-1}$ (-OH)
3020 cm$^{-1}$ (-$CH_3$)
1630 cm$^{-1}$ (-$CH=CH_2$)

$^1$H NMR spectrum:

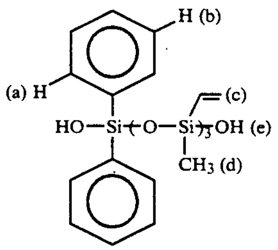

| δ (ppm) | Assignment |
|---|---|
| 7.6 (4H) | a |
| 7.2 (6H) | b |
| 6.0 (9H) | c |
| 0.1 (9H) | d |
| 5.7-6.2 (2H) | e |

OH number: 0.31 mol/100 g (theoretical: 0.43 mol/100 g)
Refractive index $n_D^{25}$: 1.5053

EXAMPLE 6

The same procedure as in Example 1 was repeated except for using 351.5 g (1.0 mol) of 1,1,3,3,5,5,7,7-octamethyl-1,7-dichlorotetrasiloxane, 383.3 g (6.6 mol) of propylene oxide and 39.6 g (2.2 mol) of water, to obtain 283.2 g of a colorless transparent liquid.

The liquid obtained was found by the following analytical results to be 1,1,3,3,5,5,7,7-octamethyl-1,7dichlorotetrasiloxane.

Figure 6:
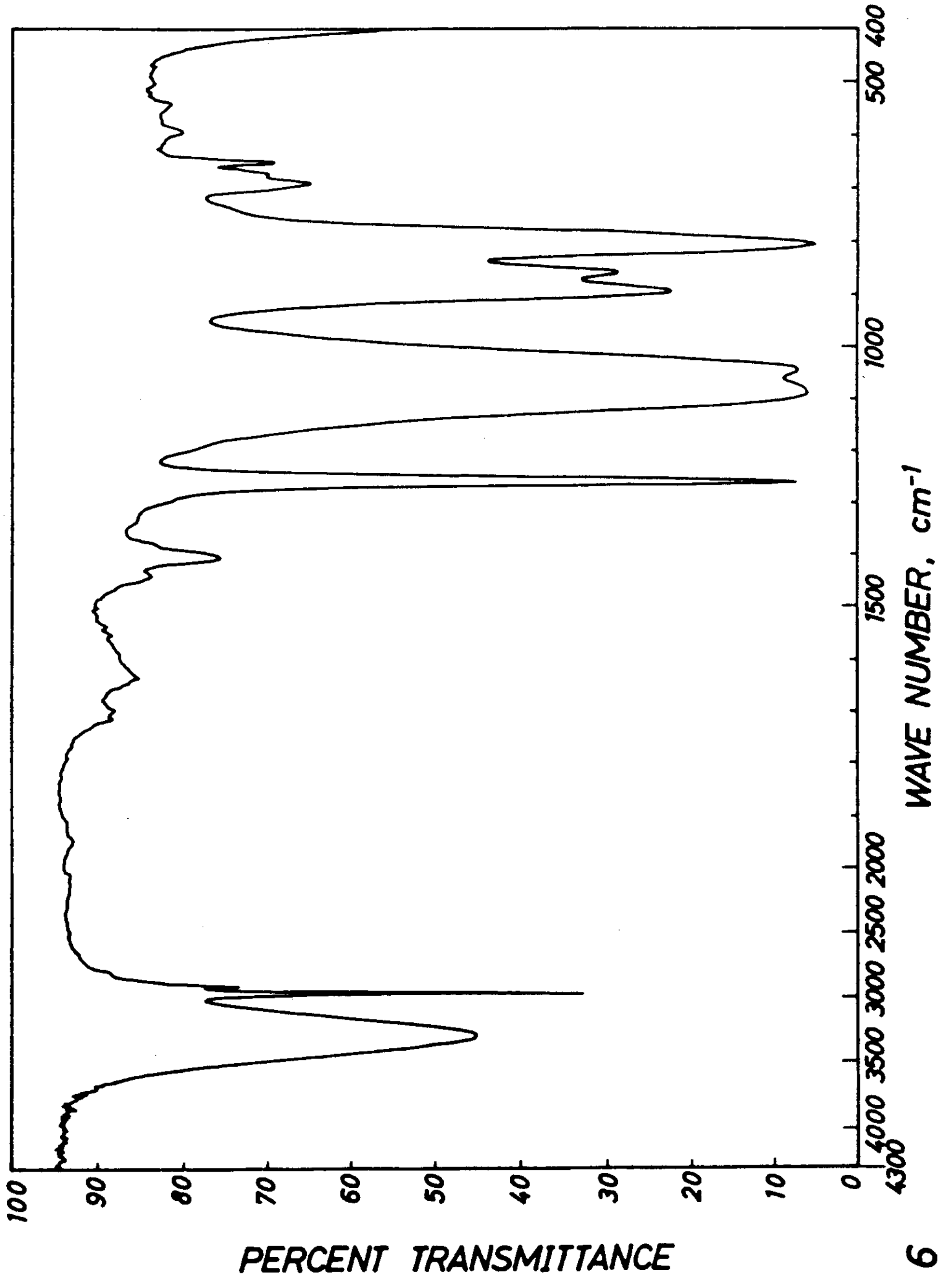

Elemental analysis:
Found: C: 30.2 %; H: 8.40 %; 0: 25.7 %; Si: 35.3 %.
Calcd. for $C_8H_{26}O_5Si_4$:
C: 30.5 %; H: 8.33 %; 0: 25.4 %; Si: 35.7 %.
IR absorption spectrum: (shown in FIG. 6)
3700-2800 cm$^{-1}$ (-OH)
2970 cm$^{-1}$ (-$CH_3$)

$^1$H NMR spectrum:

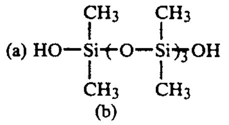

| δ (ppm) | Assignment |
|---|---|
| 5.5 (2H) | a |
| 0.1 (29H) | b |

OH number: 0.51 mol/100 g (theoretical: 0.64 mol/100 g)
Refractive index $n_D^{25}$: 1.4064

EXAMPLE 7

The procedure of Example 6 was repeated except for using 475.9 g (6.6 mol) of butylene oxide in place of propylene oxide, to obtain 280.5 g of colorless transparent liquid.

The liquid obtained was found by analytical results to be identical with 1,1,3,3,5,5,7,7-octamethyl-1,7-dihydroxytetrasiloxane as obtained in Example 6.

Example 8

The procedure of Example 6 was repeated except for using 284.1 g (3.3 mol) of butadiene diepoxide in place of propylene oxide, to obtain 290.0 g of colorless transparent liquid.

The liquid obtained was found by analytical results to be identical with 1,1,3,3,5,5,7,7-octamethyl-1,7-dihydroxytetrasiloxane as obtained in Example 6.

We claim:

1. A process for producing an organotetrasiloxane having the general formula (I):

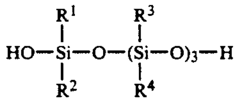

(I)

wherein $R^1$, $R^2$, $R^3$ and $R^4$, which may be identical or different, each represent a univalent substituted or unsubstituted hydrocarbon radical of 1 to 10 carbon atoms, which process comprises the step of hydrolyzing a dihalotetrasiloxane having the general formula (II):

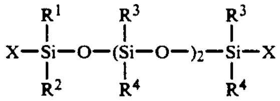

(II)

wherein $R^1$, $R^2$, $R^3$ and $R^4$ are as defined above and X represents a halogen atom, in the presence of an organic compound having at least one epoxy radical.

2. The process according to claim 1, wherein said dihalotetrasiloxane is the compound of the general formula (I) wherein $R^1$, $R^2$, $R^3$ and $R^4$ are each a radical selected from the group consisting of alkyl radicals of up to 8 carbon atoms, cycloalkyl radicals, alkenyl radicals, aryl radicals, aralkyl radicals and radicals corresponding to these radicals in which a part or all of the hydrogen atoms are substituted by halogen atoms, and X is a chlorine atom.

3. The process according to claim 1, wherein said organic compound having at least one epoxy radical is used in an amount of at least 1 mol per mol of the Si-X radicals in the dihalotetrasiloxane.

4. The process according to claim 3, wherein said organic compound having at least one epoxy radical is used in an amount of from 3.0 to 4.0 mol per mol of the Si-X radicals in the dihalotetrasiloxane.

5. The process according to claim 1, wherein said organic compound having at least one epoxy radical is at least one compound selected from the group consisting of propylene oxide, butylene oxide, epichlorohydrin and butadiene diepoxide.

6. The process according to claim 5, wherein the organic compound having at least one epoxy radical is propylene oxide.

7. The process according to claim 1, wherein the hydrolysis is carried out under the condition of pH 6 to 8.

* * * * *